United States Patent [19]
Juvinall et al.

[11] Patent Number: 5,896,195
[45] Date of Patent: Apr. 20, 1999

[54] CONTAINER SEALING SURFACE AREA INSPECTION

[75] Inventors: John W. Juvinall, Ottawa Lake, Mich.; James A. Ringlien, Maumee, Ohio; William T. Shepherd, Evans City, Pa.

[73] Assignee: Owens-Brockway Glass Container Inc., Toledo, Ohio

[21] Appl. No.: 08/856,829

[22] Filed: May 15, 1997

[51] Int. Cl.$^6$ .................................................. G01N 21/00
[52] U.S. Cl. .................. 356/240.1; 356/428; 250/223 B
[58] Field of Search ...................................... 356/237, 240, 356/375, 376, 240.1, 237.1, 428; 250/223 B

[56] References Cited

U.S. PATENT DOCUMENTS

| | | |
|---|---|---|
| 3,313,409 | 4/1967 | Johnson . |
| 3,788,741 | 1/1974 | Buechler . |
| 3,880,750 | 4/1975 | Butler et al. . |
| 4,198,164 | 4/1980 | Cantor . |
| 4,376,951 | 3/1983 | Miyazawa . |
| 4,378,493 | 3/1983 | Dorf et al. . |
| 4,476,533 | 10/1984 | Daudt et al. . |
| 4,694,158 | 9/1987 | Leser . |
| 4,762,544 | 8/1988 | Davey . |
| 4,811,251 | 3/1989 | Minato . |
| 4,906,098 | 3/1990 | Thomas et al. . |
| 4,945,228 | 7/1990 | Juvinall et al. . |
| 4,958,223 | 9/1990 | Juvinall et al. . |
| 5,020,908 | 6/1991 | Hermann . |
| 5,085,516 | 2/1992 | Bertrand et al. . |
| 5,249,034 | 9/1993 | Minato . |
| 5,489,987 | 2/1996 | Ringlien . |

FOREIGN PATENT DOCUMENTS

| | | |
|---|---|---|
| 0331290A2 | 9/1989 | European Pat. Off. . |
| 0698776A2 | 2/1996 | European Pat. Off. . |
| 59-65243 | 4/1984 | Japan . |
| 63-228049 | 9/1988 | Japan . |

*Primary Examiner*—Robert Kim
*Assistant Examiner*—Amanda Merlino

[57] ABSTRACT

Apparatus for inspecting the sealing surface area of a container finish that includes a structured light source positioned to direct a collimated line-shaped light beam onto the sealing surface area of a container as the container is moved relative to the light source. The line-shaped light beam at the container sealing surface area has a long dimension orthogonal to the container axis that extends chordally across the sealing surface area, and a narrow dimension tangential to the container axis. A light sensor is disposed to receive portions of the line-shaped light beam reflected from the sealing surface area, and provides an electrical output signal that varies with height or level of the sealing surface with respect to the light source and sensor. The sensor is coupled to associated electronics for providing information indicative of sealing surface height. The elongated dimension of the line-shaped light beam at the container sealing surface area accommodates wobble or misalignment at the sealing surface with respect to the light source and sensor. Furthermore, the elongated radial dimension of the line-shaped light beam at the container sealing surface area produces a reflection on the sensor from any wire-edge or over-press within the container mouth, thus producing at the sensor information indicative of both existence and height of any such wire-edge or over-press.

14 Claims, 4 Drawing Sheets

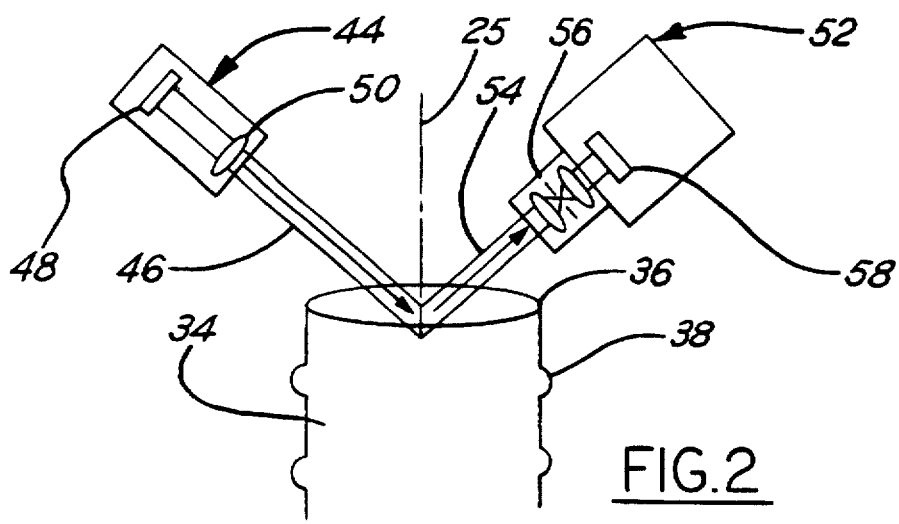
FIG.2
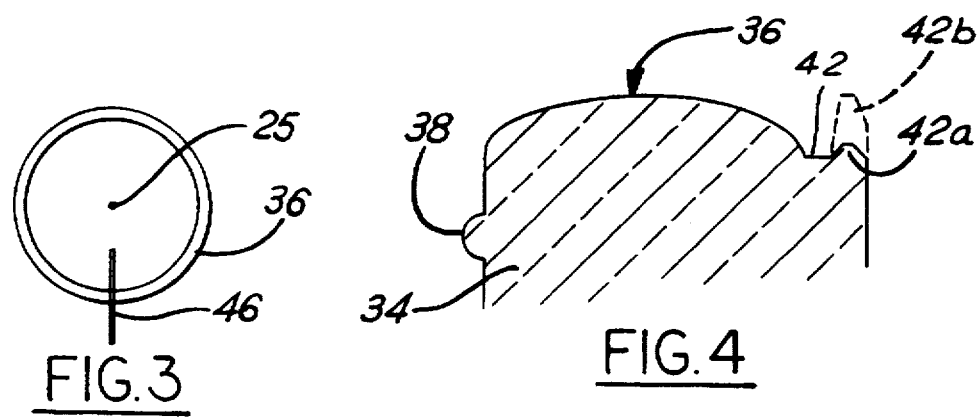
FIG.3
FIG.4
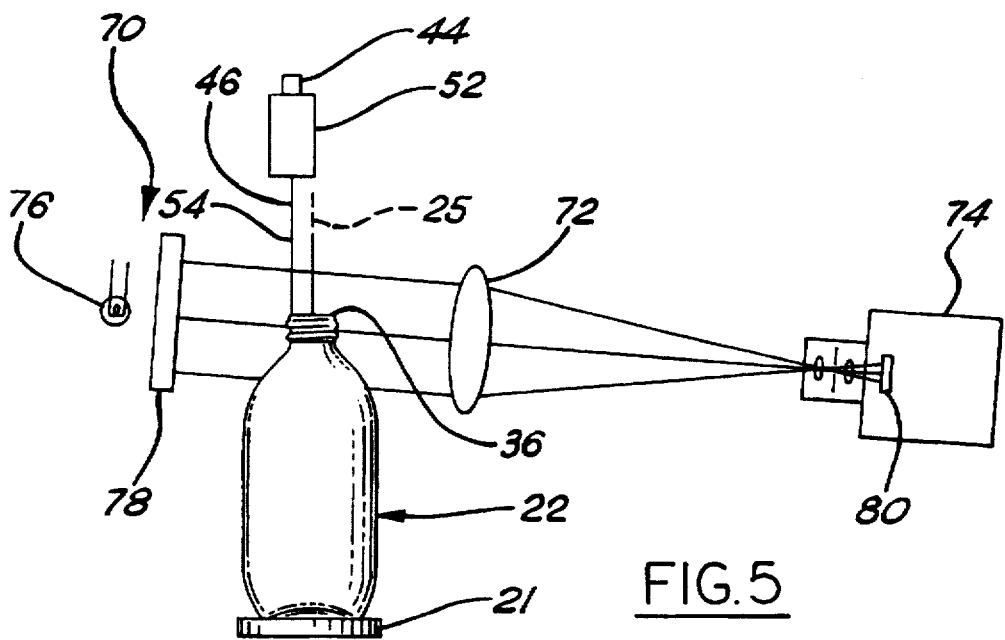
FIG.5

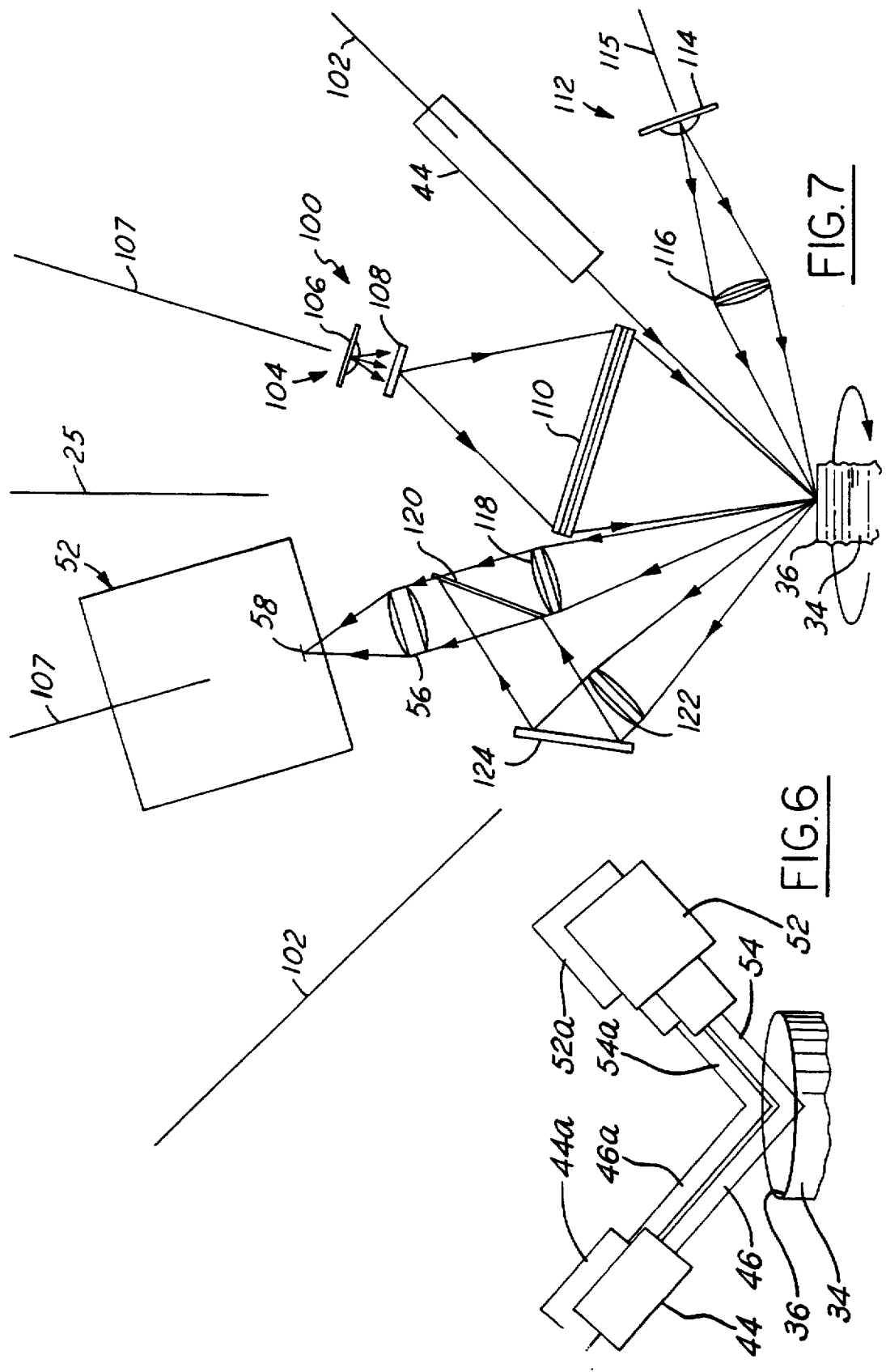

CONTAINER SEALING SURFACE AREA INSPECTION

The present invention is directed to inspection of containers, and more particularly to a method and apparatus for detecting commercial variations at the sealing surface area of a container.

BACKGROUND AND OBJECTS OF THE INVENTION

U.S. Pat. No. 3,313,409 discloses an apparatus for inspecting glass containers in which a starwheel conveys containers in sequence through a series of inspection stations. At one of the inspection stations, selected dimensional parameters of each container are inspected by contacting the container with rollers coupled to sensors, and rotating the container about its central axis so that the sensors provide output signals that vary as a function of variation of the container parameters. Specifically, container height, sealing surface warp and dip, and cocked orientation of the container finish are measured by rollers that engage the container sealing surface as the container rotates. The rollers are coupled to LVDT sensors that provide analog electrical signals indicative of deviations or variations in height (level) at the sealing surface. These signals are fed to appropriate electronics to energize a reject plunger for separating a container from the conveyor line if the measurement signals depart from desired standards and specifications. The rollers in contact with the container sealing surface are subject to mechanical wear, and can cause contamination at the sealing surface. Furthermore, the size of the rollers limits the size of containers in connection with which they may be employed, and the size (resolution) of height variations that can be detected. The moving parts require maintenance and repair. Furthermore, the roller construction is not adapted to measure height of any wire-edge or over-press within the sealing surface lip.

U.S. Pat. No. 4,945,228 discloses an apparatus for inspecting the sealing surface of a container finish that includes a light source positioned to direct light energy onto the container sealing surface as the container is held in stationary position and rotated about its central axis. A camera, which includes a linear array or matrix (area) array of light sensitive elements, is positioned and oriented with respect to the container axis of rotation to receive light energy reflected by the sealing surface, with the camera having an effective field of view limited to an angular portion less than the entire circumference of the container sealing surface. The camera array is scanned at increments of container rotation to develop information indicative of intensity of light at each array element as a function of such increments, and commercial variations at the container sealing surface are detected as a function of such information. The apparatus so disclosed is well adapted to detect commercial variations that affect reflectivity of the container sealing surface, such as line-over-finish variations, blisters, stones and a dirty container finish. However, the apparatus so disclosed is not adapted to measure dimensional parameters of the container finish, such as height of the container sealing surface, warp, dip or cock at the container sealing surface, and/or height of any wire-edge or over-press at the sealing surface.

U.S. Pat. No. 5,489,987 discloses an apparatus for inspecting the sealing surface area of containers that includes a light source positioned to direct a narrow beam of light energy at an acute angle onto the sealing surface area of a container as the container is rotated about its central axis. A light sensor is disposed to receive the narrow beam of light energy reflected from the sealing surface area, and provides an output signal that varies as a function of position of incidence of the reflected light beam on the sensor. That is, the reflected light beam is incident on the sensor at a position that varies with height or level of the sealing surface with respect to the light source and sensor, and the sensor is characterized by providing an electrical output signal that varies as a function of position of incidence of the reflected light beam on the sensor. Variations in height at the sealing surface area are detected as a function of the sensor output signal. In one embodiment, light source/sensor pairs are disposed on diametrically opposed sides of the container axis, and warp, dip and/or cock at the sealing surface of the container is detected as a combined function of variations in position of incidence of the reflected light beams on the sensors as the container rotates.

It is a general object of the present invention to provide an improved apparatus and method for inspecting the sealing surface area of containers for unacceptable commercial variations or defects. Another and more specific object of the present invention is to provide an apparatus and method of the described character that are adapted to inspect the sealing surface area of a container for multiple types of variations in a single operation and at a single inspection station. A further object of the present invention is to provide a method and apparatus of the described character for inspecting both optical and dimensional characteristics of the sealing surface area of a container finish.

It is another object of the present invention to provide an apparatus and method for measuring or determining dimensional characteristics of a container finish, particularly a container sealing surface area, of the type disclosed in the above-noted U.S. Pat. No. 5,489,987, in which the measurement process is characterized by improved immunity to positional variations or wobble at the container sealing surface. Another object of the present invention is to provide a method and apparatus of the described character that attains the foregoing objective while being economical to implement and reliable over an extended operating lifetime. Yet another and more specific object of the present invention is to provide an electro-optical non-contact method and apparatus for measuring height characteristics at the sealing surface of a container, particularly warp, dip and/or cock at the container finish and sealing surface, that in part employ electro-optics already provided for measuring other dimensional parameters at the container finish. A further object of the present invention is to provide a method and apparatus of the described character that, in alternative embodiments, may be implemented at either the hot end or the cold end of a glassware manufacturing system.

SUMMARY OF THE INVENTION

Apparatus for inspecting the sealing surface area of a container finish in accordance with one aspect of the present invention includes a structured light source positioned to direct a collimated line-shaped light beam (i.e., having a length dimension many times a width dimension) onto the sealing surface area of a container. The line-shaped light beam at the container sealing surface area has a long dimension orthogonal to the container axis, and a narrow dimension tangential to the sealing surface. A light sensor is disposed to receive portions of the line-shaped light beam reflected from the sealing surface area, and provides an electrical output signal that varies with height or level of the sealing surface area with respect to the light source and sensor. The sensor is coupled to associated electronics for providing information indicative of sealing surface height. In the preferred embodiments, multiple images are obtained at the sensor from different portions of the sealing surface, either by moving the sealing surface area relative to the light source and sensor between images, or by employing multiple laser lines and reflections from the sealing surface. The elongated dimension of the line-shaped light beam at the container sealing surface accommodates wobble or misalignment at the sealing surface with respect to the light source and sensor. Furthermore, the elongated radial dimension of the line-shaped light beam at the container sealing surface also produces a reflection on the sensor from the wire-edge within the container mouth, thus producing at the sensor information indicative of both existence and height of any such wire-edge, and whether height of the wire-edge exceeds height of the sealing surface—i.e., an over-press.

The light source and sensor in the preferred embodiments of the invention are disposed above the sealing surface area of the container, and are oriented with respect to each other and with respect to the container sealing surface area such that portions of the light beam incident on and reflected from the container sealing surface area are nominally at a 90° angle with respect to each other, and nominally in a plane perpendicular to the sealing surface. (The term "nominal" refers to conditions that prevail at the ideal or design height and orientation of the sealing surface, any departure from such ideal height and orientation due to a short container or wobble at the container finish potentially causing minor departure from the "nominal" reflected beam orientation and angle.) The light source and sensor are disposed in a plane nominally parallel to the container axis and perpendicular to the sealing surface. The light sensor in the preferred embodiments of the invention includes a matrix (i.e., area) array sensor, and one or more lenses for focusing onto the sensor the light energy reflected from the container sealing surface area. The focusing lenses have an image plane at the matrix array sensor and an object plane nominally coincident with the line-shaped light beam at the container sealing surface. The acceptance angle of the light sensor lenses preferably is limited radially of the container sealing surface so that only light reflected from nearly horizonal portions of the sealing surface are directed onto the sensor. The acceptance angle of the sensor lenses preferably is wide tangentially of the sealing surface to receive the light even if the container is tilted slightly, or has a rough sealing surface that tends to disperse the reflected energy. In the preferred embodiments of the invention, the sealing surface light source comprises a laser diode and lenses for projecting light from the laser diode as a laser line onto the container sealing surface.

In one embodiment of the invention, a second light sensor includes a second matrix array sensor and a telecentric lens for focusing onto the second sensor an image of the container finish profile formed by light energy parallel to the axis of the telecentric lens. This second light sensor views a different portion of the container finish from that viewed by the first sensor, and at a slight downward angle with respect to the sealing surface area. The output information from the first or sealing surface sensor and the second or profile sensor is monitored as a function of rotation of the container for determining warp, dip and/or cock of the container finish. The second light sensor (in addition to being able to measure dimensional parameters of the container finish) allows isolation of up and down motion of the container as a whole from determination of warp, dip and cock. In another modified embodiment, the first light sensor is combined either with another laser-line light source, or with a narrow-beam light source as in the above-referenced application, diametrically opposed to the first light source and sensor across the container mouth. The outputs of the two light sensors are combined to measure warp, dip and/or cock at the sealing surface.

Apparatus for inspecting the finish of a container in accordance with another aspect of the present invention includes first and second light sources for directing light energies onto the sealing surface area of a container from differing angles with respect to the container axis and the nominal plane of the sealing surface. Light energy reflected from the sealing surface area of the container from the first and second light sources is directed onto a matrix array sensor, such that the sensor effectively views the container sealing surface area from two differing angles corresponding to the angles of illumination from the light sources. In the preferred implementation of this aspect of the invention, the differing light sources are of differing structure for illuminating the container sealing surface with light having differing properties as well as differing illumination angles for detecting differing physical and/or dimensional characteristics of the container sealing surface. The differing light sources are alternately energized, preferably at increments of container rotation, and the sensor is scanned to develop sequential images of differing sealing surface characteristics.

In the preferred implementation of this second aspect of the invention, three structured light sources direct light energies of differing characteristics onto the container sealing surface at differing angles, a first for inspecting the sealing surface for characteristics that affect reflectivity of the sealing surface, a second for inspecting the step-down for a wire edge or an overpress condition, and a third for detecting crizzle in the step-down area at the inner edge of the sealing surface. A pair of lenses are positioned to intercept light energy reflected by the sealing surface from the first and second light sources. The lenses are positioned so as to have a first focus disposed at the sealing surface such that the reflected light energy is collimated by passage through the lenses. The collimated light energy is incident on a beam splitter for combining the reflected energy beams along a single path onto the matrix array sensor. The light energy reflected from the sealing surface from the third light source normally is not incident on the sensor. However, any fractured glass crizzle scatters the light energy so that a portion will be reflected through the lenses onto the matrix array sensor.

BRIEF DESCRIPTION OF THE DRAWINGS

The invention, together with additional objects, features and advantages thereof, will be best understood from the following description, the appended claims and the accompanying drawings in which:

FIG. 2 is fragmentary schematic diagram that illustrates operation of the embodiment illustrated in FIG. 1;

FIG. 3 is a top plan view of the embodiment illustrated in FIGS. 1 and 2 showing orientation of the light beam with respect to the container sealing surface and container axis;

FIG. 4 is a fragmentary sectional view on an enlarged scale of a container sealing surface area;

FIGS. 5 and 6 are schematic diagrams of respective modified embodiments of the invention;

FIG. 7 is a schematic diagram of apparatus for inspecting the sealing surface of containers in accordance with a further aspect of the present invention.

DETAILED DESCRIPTION OF PREFERRED EMBODIMENTS

Figure 1:
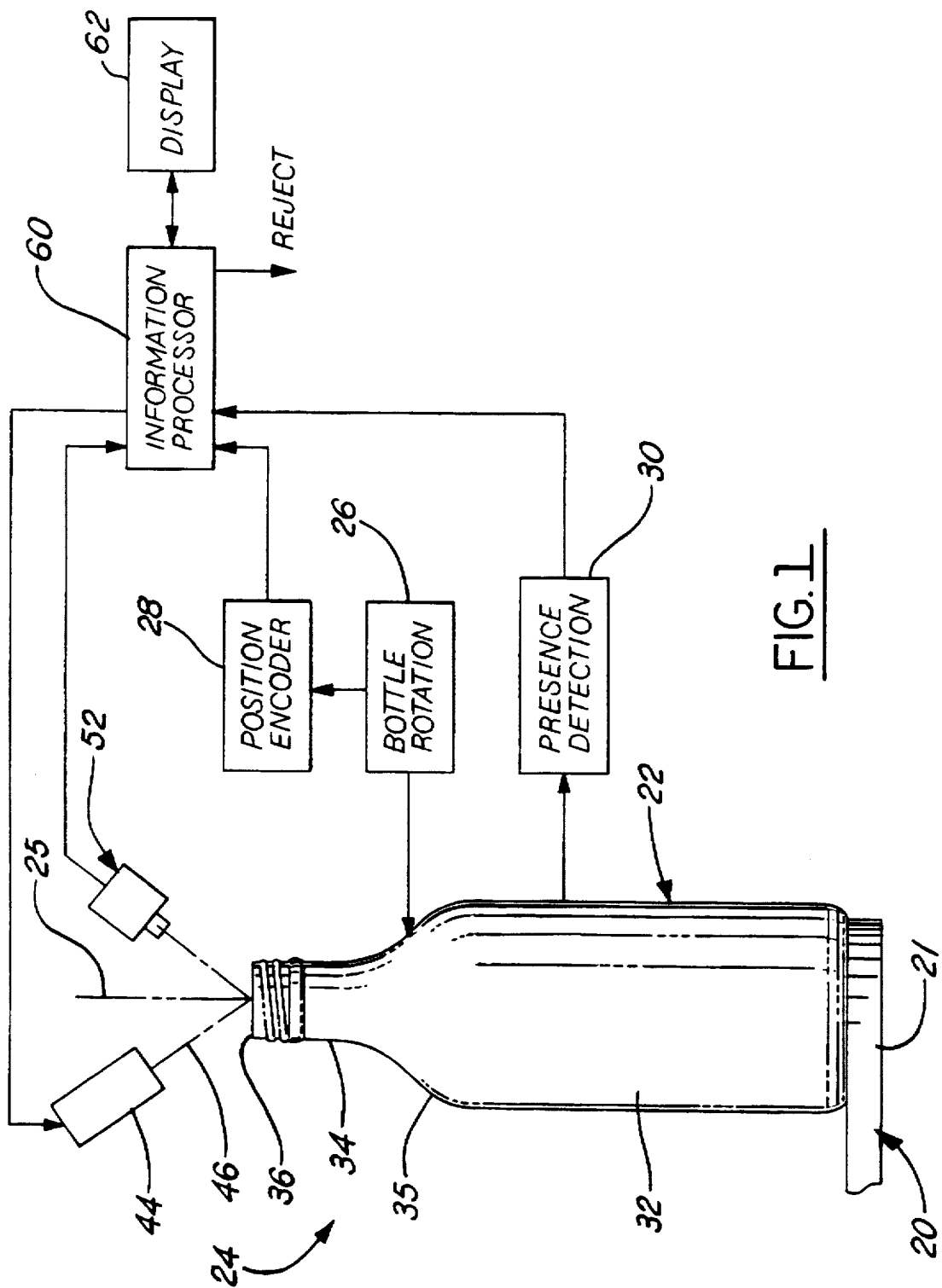
FIG. 1 is a schematic diagram of apparatus for inspecting the sealing surface area of containers in accordance with one presently preferred embodiment of the invention.

Referring to FIG. 1, a conveyor 20, typically including a starwheel and a slideplate 21, is so disposed and connected to a source of molded containers as to bring successive containers 22 into position at a sealing surface inspection station 24. Such a starwheel conveyor container inspection arrangement is disclosed, for example, in above-noted U.S. Pat. No. 3,313,409. A bottle-rotating device 26, such as a drive roller, is positioned to engage each container 22 in sequence at station 24, and to rotate the container about its central axis 25 as the container is held in fixed position by the conveyor. An encoder 28 is coupled to the container rotation mechanism to provide signals indicative of increments of container rotation. Such container rotation increments may comprise fixed increments of angular position, or fixed time increments as the container is rotated at constant velocity. A detector 30, such as a switch, is positioned to provide a signal indicative of presence of container 22 at station 24.

In the implementation of the present invention illustrated in FIG. 1, container 22 comprises a molded glass bottle having a cylindrical body 32 and a generally cylindrical neck 34 that projects upwardly from the body shoulder 35. The finish portion of the container includes an upper portion of neck 34 that terminates in an axially facing cap sealing surface 36, which is inspected in accordance with the present invention. A helical thread 38 is integrally molded into the outer surface of the finish wall that surrounds the container mouth, and a lip or shoulder 40 is formed on the finish wall outer surface over which a cap skirt may be crimped in the usual manner for affixing the cap to the container. A step-down 42 (FIG. 4) may exist around the inside diameter of sealing surface 36 due to characteristics of the mold in which the container was formed. Excessive height at step-down 42 becomes a wire-edge 42a. When the wire-edge exceeds the height of the sealing surface 36, it becomes an overpress 42b. A wire-edge or an overpress is undesirable for a number of reasons, and may indicate a problem at the container mold. The embodiment of the invention illustrated in FIG. 1 is directed to a method and apparatus for inspecting height or level at sealing surface 36 and step-down 42. In this connection, it will be appreciated as the description unfolds that the term "sealing surface" in the present application refers to the entire sealing surface area including not only the sealing surface proper 36, but also the step-down 42.

A light source 44 is positioned above sealing surface 36 of container 22 at station 24, and oriented to direct a narrow collimated beam 46 of light energy downwardly at an acute angle onto sealing surface 36. Specifically, light beam 46 comprises a collimated line-shaped light beam that has a long dimension at sealing surface 36 orthogonal to and coplanar with container axis 25 at the nominal position and orientation of container 22 at station 24, and a narrow dimension tangential to the container axis. Light source 44 may comprise a laser diode 48 and cylindrical lenses 50 for forming the collimated line-shaped laser beam as described. A camera 52 is positioned above sealing surface 36 of container 22 at station 24, and oriented to receive that portion 54 of beam 46 reflected from sealing surface 36 (and step-down 42, if any). Camera 52 includes a focusing lens arrangement 56 and a matrix (area) array light sensor 58 onto which lenses 56 focus reflected light energy 54. Light source 44 and camera 52 are disposed in the plane of incident light beam 46 and reflected light beam 54, which plane is parallel to and laterally offset from container axis 25. The angle of incidence of illumination beam 46, and the nominal angle of reflection of beam 54, are each at 45° with respect to axis 25, which is to say that beams 46, 54 are at a nominal angle of 90° with respect to each other.

An information processor 60 (FIG. 1) receives signals from detector 30 indicating presence of a container at inspection station 24, and signals from encoder 28 indicative of increments of container rotation. Camera 52 is likewise coupled to information processor 60 for receiving control signals from processor 60, and for providing output signals to the information processor indicative of position of incidence of reflected light energy 54 on sensor 58. Light source 44 is likewise controlled by processor 60. Processor 60 is also connected to a display 62 for displaying image data to an operator, and provides a reject signal to a suitable mechanism for removing unacceptable containers from the conveyor line.

In operation of the embodiment of the invention illustrated in FIGS. 1–4, line-shaped illumination beam 46 intersects sealing surface 36, and a portion thereof is reflected by the horizontal portion of sealing surface 36 onto sensor 58 in camera 52. Likewise, a portion of the illumination beam is reflected from wire-edge 42 onto camera sensor 58. Camera lenses 56 preferably have an image plane disposed at the imaging surface of matrix array sensor 58, and an object plane collinear with beam 46 at the nominal position of sealing surface 36. If the sealing surface is not horizontal due to tilting, lenses 56 still image the reflected light energy, so that tilting at the sealing surface does not affect the image at array sensor 58 and the height measurement signals provided thereby. The acceptance angle of lenses 56 is limited in the direction radial to sealing surface 36 so that only light energy that reflects from the nearly horizontal portions of the sealing surface are directed onto sensor 58. Lenses 56 have a wide acceptance angle in the direction tangential to axis 25 and sealing surface 36 so as to allow the reflected light energy to be directed onto sensor 58 even if the sealing surface is misaligned laterally of the nominal position or tilted slightly, or if the light energy is reflected from a rough portion of the sealing surface.

From the image(s) projected onto sensor 58, height of sealing surface 36 and step-down 42 (if any) can be determined by information processor 60 as a function of relative positions of incidence at sensor 58. Since sealing surface 36 typically is crowned (FIG. 4) and step-down 42 is fairly narrow, the reflected light image at camera 52 will typically consist of two bright spots, one created by the small amount of light reflected by the point of the sealing surface perpendicular to the plane of the light beams, and one from the tip of the wire-edge. The relative positions of these two image spots provide the desired information.

Information regarding warp and dip at the container sealing surface can be obtained with the embodiment of the invention illustrated in FIGS. 1–4. However, overall container wobble would affect these measurements. FIG. 5 illustrates a modified embodiment of the invention in which light source 44 and camera 52 from the embodiment of FIGS. 1–4 are combined with a light source 70, a telecentric lens 72 and a camera 74. Light source 70 includes a lamp 76 and a diffuser 78 for illuminating the finish 34 of container 22. Telecentric lens 72 directs onto a matrix (area) array sensor 80 of camera 74 only light rays that are parallel to the axis of telecentric lens 72, which is at a slight angle (e.g., 5°) beneath the body of the sealing surface so as to view only a near edge of the sealing surface. Cameras 52, 74 view diametrically opposed sides of the sealing surface. Thus, a sharp image of container finish 34 is directed onto sensor 80 of camera 74. This image can be analyzed for obtaining profile dimensional information in accordance with the disclosure of U.S. application Ser. No. 08/296,297 filed Aug. 25, 1994. This profile dimensional information can also be combined with sealing surface height information obtained at camera 52 for determining warp, dip and/or cock at the container finish substantially independent at container wobble and overall variations in container height. That is, the information obtained at camera 74 provides reference information indicative of overall sealing surface height, to which incremental height measurements at camera 52 are referenced as a function of container rotation for determining overall warp, dip and/or cock characteristics of the container sealing surface.

FIG. 6 illustrates another embodiment of the invention, in which a second laser-line light source 44a is disposed to direct a light beam 46a onto sealing surface 36, from which a beam 54a is reflected to a second camera 52a. Light source/camera pairs 44, 52 and 44a, 52a operate upon diametrically opposed sides of sealing surface 36. The outputs of cameras 52, 52a may be combined at information processor 60 (FIG. 1) to determine warp, dip and/or cock at the sealing surface as disclosed in above-referenced U.S. Pat. No. 5,489,987. Secondary light source 44a and camera 52a may be explained by a narrow beam light source and camera as disclosed in the referenced application.

FIG. 7 illustrates apparatus 100 for performing several inspections on the sealing surface 36 of a container finish 34 in accordance with another aspect and embodiment of the invention. A first light source 44 is positioned at an angle 102 for directing a line-shaped light beam onto sealing surface 36 as previously described. A second light source 104 includes an LED 106 that transmits a light beam at an angle 107 through a diffuser 108 and a fresnel lens arrangement 110 onto sealing surface 36 at the point of intersection of the light beam from laser diode light source 44. A third light source 112 includes an LED 114 that directs light energy at an angle 115 onto sealing surface 36, again to intersect the sealing surface at the point of illumination from light sources 44, 104. Camera 52 is disposed at angle 107 on the opposing side of container axis 25. Light energy normally reflected from light source 104 is incident on a lens 118. This lens is mounted at a distance from sealing surface 36 equal to its focal length from the point of illumination, so that the reflected light energy traveling through the lens is collimated. Such collimated light energy is directed through a beam splitter 120 and lenses 56 onto matrix array sensor 58 in camera 52. A lens 122 is positioned at angle 102 opposite light source 44, and again is mounted at a distance from the point of illumination at sealing surface 36 equal to its focal length. The collimated light energy that has passed lens 122 is directed by a mirror 124 onto beam splitter 120, from whence such reflected light energy is directed through lens 56 onto matrix array sensor 58. Thus, lenses 118, 122, mirror 124 and beam splitter 120 function to combine the light energy from light sources 44, 104 reflected from sealing surface 36 onto a single beam path directed onto matrix array sensor 58. Angle 115 of light source 112 is such that the light energy therefrom is normally reflected by sealing surface 36 away from camera 52. Exemplary values for angles 102, 107, 115 with respect to axis 25 are 45°, 17° and 70° respectively.

The point on sealing surface 36 illuminated by light source 104 receives light energy coming from the entire aperture of fresnel lens arrangement 110. After reflection, this light is directed by lenses 118, 56 onto matrix array sensor 58. A bright image of the sealing surface as illuminated by light from the fresnel lenses is formed on the array. Strongly sloped regions of the sealing surface, such as the edges of a line-over-finish variation, pits, etc., will appear as dark areas against this bright image background since such areas reflect light energy away from lens 118. Using a matrix array sensor 58, orientation and shape of the feature is relatively unimportant.

As in the prior embodiments, only those portions of the sealing surface that are nearly horizontal reflect energy from light source 44 through lenses 122, 56 onto matrix array sensor 58, where such areas appear as bright spots on an otherwise dark background. Due to the included angle of 90° between the illumination axis and the viewing axis, image processor 60 (FIG. 1) can determine if the highlight from the step-down, if present, is above or below the sealing surface. If the step-down is above the sealing surface, an overpress condition is indicated. If the wire edge is below the sealing surface or not present, no overpress is indicated. As noted above, light source 112 functions in combination with matrix array sensor 58 of camera 52 to detect crizzle, which is a condition in which the inner edge or step-down area 43 (FIG. 4) of the sealing surface is broken up or has numerous cracks. If step-down area 42 is smooth and free of crizzle, the light energy from light source 112 is reflected by the sealing surface away from lenses 122, 118 and camera 52. Fractured glass of crizzle will scatter (refract or reflect) some of the light energy toward lenses 118, 122 and onto array sensor 58. The crizzle thus appears as a bright image against an otherwise dark background.

In operation, the three light sources 44, 104, 112 are strobed in sequence, and matrix array sensor 58 is scanned by information processor 60 at each light source strobe. For example, a first frame scanned from matrix array sensor 58 may receive an image by flashing of light source 104, a second frame by flashing light source 44, a third frame by flashing light source 104 again, and a fourth frame by flashing light source 112. In this way, four frames of data are taken from the camera, each with its own illumination. This process is repeated rapidly at increments of container rotation for developing multiple two-dimensional images of the container sealing surface. Since the light sources are disposed at differing angles to the sealing surface, and lenses are employed for directing reflected energy from these light sources onto a single matrix array sensor, the single sensor effectively views the sealing surface from multiple angles. Furthermore, all of the optics of FIG. 7 can be incorporated into a single inspection station.

Figure 8:
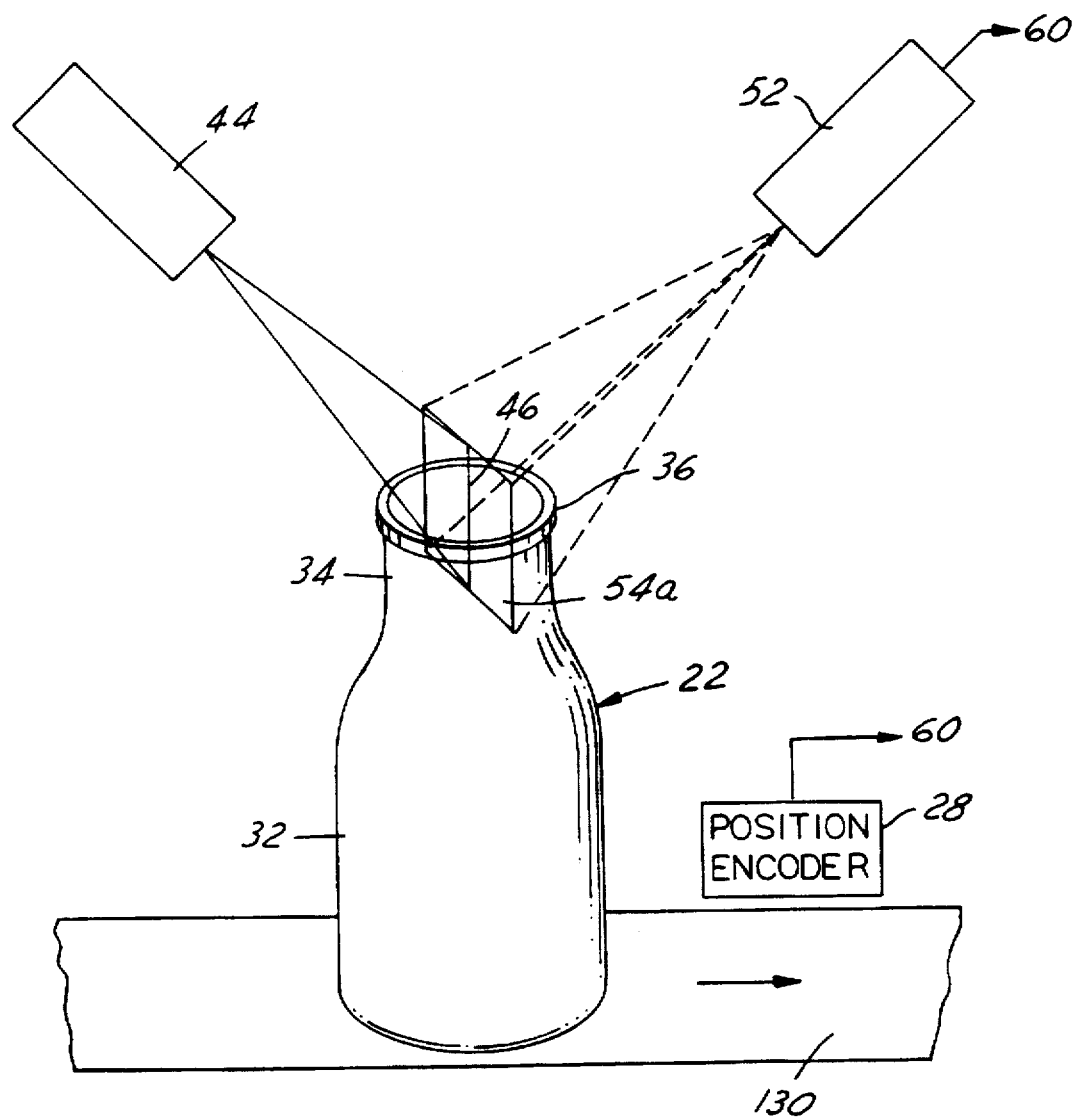
FIG. 8 is a schematic diagram of apparatus for inspecting containers in accordance with the invention at the so-called hot end of the manufacturing process.

In the embodiment of FIGS. 1–7, relative motion between the light source/sensor systems and the container is obtained by a roller 26 (FIG. 1) or the like that contacts the container and rotates the container about its axis 25. Such a technique is suitable for use at the so-called cold end of a glassware manufacturing process—i.e., downstream of the annealing lehr—where the containers are cool and rigid. However, such a technique would not be suitable for use at the so-called hot end of the manufacturing process—i.e., between the glassware manufacturing machine and the annealing lehr—because the roller would distort the hot and pliable container sidewall. FIG. 8 illustrates a hot container 22 being transported on an endless belt conveyor 130 between the manufacturing machine and the annealing lehr. Position encoder 28 is coupled to conveyor 130 to provide signals to information processor 60 (FIG. 1) indicative of conveyor/container motion. Information processor 60 scans camera 52 at increments of linear container motion so as to obtain multiple images of reflections of light beam 46 from the sealing surface area. For example, camera 52 may be scanned to obtain ten images in which the laser line extends chordally across the sealing surface area. Reflections from the sealing surface area will appear as bright spots against an otherwise dark background. Note that the image plane 54a of the matrix array sensor within camera 52 extends above and below the nominal height of sealing surface area 36, which will accommodate substantial variations in wobble or height.

As noted above, multiple reflections preferably are obtained from different areas of the sealing surface of a container. This is accomplished either by causing relative motion between the light source/sensor system and the container between scan images (rotating in FIGS. 1–7 and translation in FIG. 8), or by illuminating the sealing surface area with multiple laser lines simultaneously. The single-line/multiple-scan approach allows for a shallow depth of focus and a correspondingly larger camera lens aperture. A larger lens aperture increases the probability of a reflection from the container being intercepted by the lens. The advantage of the multiple-lens/single-image approach is that the effects of container motion will not distort the finish profile.

Information obtained from the inspection process preferably is employed to implement adjustments or corrections in the manufacturing process to overcome any problems. The adjustments or corrections could be made manually or, more preferably, automatically. When inspection is conducted at the cold end, automatic correction may be implemented as disclosed in U.S. Pat. No. 4,762,544. Most preferably, inspection is performed at the hot end and appropriate parameters in the manufacturing process are automatically adjusted. For correction of warp, dip, cock, height variations and/or ware-edge overpress, adjustments are made to machine timing, cooling and/or gob characteristics. Persistent problems may also indicate a need for machine, section or mold maintenance or repair.

We claim:

1. Apparatus for inspecting the finish of a container having a central axis and an open mouth surrounded by an axially facing sealing surface area, said apparatus comprising:

first and second light sources for directing light energy onto the sealing surface area of a container from respective differing angles with respect to said axis, light sensor means including a matrix array sensor and means for directing light energy reflected from the sealing surface area from both of said light sources onto said matrix array sensor such that said sensor views the sealing surface area from at least said differing angles, means coupled to said first and second light sources and to said matrix array sensor for scanning said sensor to obtain two-dimensional images of the container sealing surface area as said first and second light sources are respectively energized, and means for detecting commercial variations at the sealing surface area of a container as a function of said two-dimensional images.

2. The apparatus set forth in claim 1 further comprising means coupled to said first and second light sources for alternately energizing said first and second light sources so as to direct light energy onto the sealing surface area alternately from said differing angles.

3. The apparatus set forth in claim 2 wherein said means for directing light energy onto said sensor comprises a pair of lenses having axes at differing angles to the sealing surface area and respective foci at the sealing surface area such that light energy reflected from the sealing surface area is collimated after passage through said lenses, a beam splitter disposed to direct the collimated light energy from said lenses along a single path, and means for directing such energy on said single path onto said matrix array sensor.

4. The apparatus set forth in claim 2 wherein said first and second light sources are alternately strobed.

5. The apparatus set forth in claim 2 wherein one of said light sources comprises a fresnel lens arrangement having a focal point at the sealing surface area.

6. The apparatus set forth in claim 1 wherein one of said light sources comprises means for directing a line-shaped light beam onto the sealing surface area of the container in such a way that the line-shaped beam at the sealing surface area has a long dimension orthogonal to the container axis and a narrow dimension tangential to the container axis, said one light source and said matrix array sensor being disposed above the sealing surface area of the container such that the light reflected by the sealing surface area of the container onto said light sensor means is incident at a position on said sensor means that varies with height of the sealing surface area with respect to said light source and said sensor means, the long dimension of said line-shaped light beam accommodating wobble or misalignment of the container sealing surface.

7. The apparatus set forth in claim 1 wherein one of said light sources is oriented such that light energy is normally reflected by the sealing surface area away from said matrix array sensor, and is reflected onto said sensor by crizzle at said sealing surface area.

8. The apparatus set forth in claim 2 wherein said first and second light sources generate light energies of respectively differing optical characteristics, said matrix array sensor alternately receiving reflected light energy from said first and second light sources as a function of differing properties of the sealing surface area of the container.

9. The apparatus set forth in claim 8 further comprising means for alternately energizing said light sources and scanning said sensor at increments of container motion.

10. The apparatus set forth in claim 9 wherein said increments comprise increment of container rotation.

11. The apparatus set forth in claim 9 wherein said increments comprises increment of linear container motion.

12. A method of inspecting the finish of a container that comprises the steps of:

(a) alternately directing light energies of differing optical characteristics at first and second differing angles onto the sealing surface area of a container finish such that said light energies are reflected at differing angles form the sealing surface area, (b) directing said light energies reflected in said step (a) onto a single matrix array sensor, (c) scanning said matrix array sensor to obtain two-dimensional images of the container sealing surface area as said first and second light sources are respectively energized, and (d) detecting commercial variations at the sealing surface are as a function of such two-dimensional images.

13. The method set forth in claim 12 wherein said step (a) comprises the steps of:

(a1) providing first and second light sources, and (a2) alternately energizing said light sources for directing light energies therefrom onto the sealing surface area from said first and second angles respectively.

14. The method set forth in claim 13 wherein said step (a1) comprises the step of structuring each of said first and second light sources to provide a different illumination light pattern at the sealing surface area.

* * * * *